(12) United States Patent
Adachi et al.

(10) Patent No.: US 6,944,261 B2
(45) Date of Patent: Sep. 13, 2005

(54) X-RAY COMPUTED TOMOGRAPHY APPARATUS

(75) Inventors: Akira Adachi, Tochigi-ken (JP); Thomas Charles Judd, Buffalo Grove, IL (US); Clay Christopher Smith, Buffalo Grove, IL (US)

(73) Assignee: Kabushiki Kaisha Toshiba, Tokyo (JP)

( * ) Notice: Subject to any disclaimer, the term of this patent is extended or adjusted under 35 U.S.C. 154(b) by 0 days.

(21) Appl. No.: 10/418,061

(22) Filed: Apr. 18, 2003

(65) Prior Publication Data

US 2004/0208275 A1 Oct. 21, 2004

(51) Int. Cl.$^7$ ................................................ G21K 5/00
(52) U.S. Cl. ............................................. 378/20; 378/4
(58) Field of Search .............................. 378/4, 19, 20, 378/8, 62, 15, 74, 12, 98

(56) References Cited

U.S. PATENT DOCUMENTS 6,341,152 B1 * 1/2002 Sugihara ...................... 378/4
6,363,134 B1 * 3/2002 Suzuki ........................ 378/15

* cited by examiner

*Primary Examiner*—David V. Bruce
*Assistant Examiner*—Hoon Song
(74) *Attorney, Agent, or Firm*—Oblon, Spivak, McClelland, Maier & Neustadt, P.C.

(57) ABSTRACT

An X-ray computed tomography apparatus including an X-ray source, a data acquisition unit, an X-ray detection unit, a reconstruction unit, a creation unit, and a display unit. An X-ray radiated toward an object by the X-ray source is detected to generate a corresponding signal by the X-ray detection unit. According to the signal, data is acquired by the data acquisition unit. A reconstruction unit reconstructs a tomographic image, while a creation unit creates a plane image based on the acquired data A display unit displays the tomographic image and the plane image.

26 Claims, 9 Drawing Sheets

X-RAY COMPUTED TOMOGRAPHY APPARATUS

FIELD OF THE INVENTION

The present invention relates to an X-ray computed tomography (CT) apparatus for playing an object image in a real time.

BACKGROUND OF THE INVENTION

Conventionally, an X-ray CT apparatus is utilized for reconstructing and displaying an object image in a real time. Although single slice CT apparatus may use for reconstructing only one tomographic image, a multi slice CT apparatus may use for simultaneously reconstructing a plurality of tomographic images in a real time. One of the multi slice CT apparatus has been disclosed in U.S. Pat. No. 6,363,134. The multi slice CT apparatus is suitable for various diagnosis, including a needle insertion diagnosis. For the needle insertion diagnosis, when an operator inserts a needle to a patient, the multi slice CT apparatus reconstructs three tomographic images in a real time. For example, a first tomographic image is placed at a tip position of a needle, a second tomographic image is placed at a middle position of the needle, and a third tomographic image is placed at an end position of the needle in order to observe a whole imaging position of the inserted needle. During this needle insertion diagnosis, the operator stands besides a patient and operates the needle, with observing a displayed image near a gantry of the CT apparatus.

However, the conventional multi slice CT apparatus can provide only vertical omographic images. Consequently, it is difficult for an operator to appropriately understand an insertion state of the needle.

SUMMARY OF THE INVENTION

The present invention intends to solve the above-mentioned problems and defects of the conventional CT apparatus. Accordingly, the present invention provides an X-ray computed tomography apparatus comprising an X-ray source configured to radiate an X-ray toward an object, an X-ray detection unit configured to detect the X-ray through the object and to generate a corresponding signal, a data acquisition unit configured to acquire data based on the corresponding signal, a reconstruction unit configured to continuously reconstruct a tomographic image of the object by a predetermined term based on the acquired data, a creation unit configured to continuously create a plane image of the object by a predetermined term based on the acquired data and a display unit configured to display the tomographic image and the plane image.

Also consistent with the present invention, there is provided an X-ray computed tomography apparatus comprising an X-ray source configured to radiate an X-ray toward an object, an X-ray detection unit configured to detect the X-ray through the object and to generate a corresponding signal, a data acquisition unit configured to acquire data based on the corresponding signal, a reconstruction unit configured to reconstruct a tomographic image of the object based on the acquired data, an input unit to input a direction of a plane image of the object, a creation unit configured to create the plane image based on the acquired data according to the direction of the plane image, and a display unit configured to display the tomographic image and the plane image.

Further consistent with the present invention, there is provided an X-ray computed tomography apparatus comprising an X-ray source configured to radiate an X-ray toward an object, an rotation unit configured to rotate a focal point of the X-ray, an X-ray detection unit configured to detect the X-ray through the object and to generate a corresponding signal, a data acquisition unit configured to acquire data based on the corresponding signal while the focal point of the X-ray rotates, a reconstruction unit configured to reconstruct a tomographic image of the object based on the acquired data, a creation unit configured to create a plane image of the object based on the acquired data, and a display unit configured to display the tomographic image and the plane image.

Still further consistent with the present invention, there is provided an X-ray computed tomography apparatus comprising an X-ray source configured to radiate an X-ray toward an object, an X-ray detection unit configured to detect the X-ray through the object and to generate a corresponding signal, a data acquisition unit configured to acquire data based on the corresponding signal, a reconstruction unit configured to reconstruct a tomographic image of the object based on the acquired data, a creation unit configured to create a plane image of the object based on the acquired data including a part of data used for the tomographic image, and a display unit configured to display the tomographic image and the plane image.

Still further consistent with the present invention, there is provided a method for controlling an X-ray computed tomography apparatus comprising radiating an X-ray toward an object by an X-ray source, detecting the X-ray through the object to generate a corresponding signal by an X-ray detection unit, acquiring data based on the corresponding signal by a data acquisition unit, continuously reconstructing a tomographic image of the object by a predetermined term based on the acquired data by a reconstruction unit, continuously creating a plane image of the object by a predetermined term based on the required data by a predetermined term by a creation unit and displaying the tomographic image and the plane image by a display unit.

BRIEF DESCRIPTION OF THE DRAWINGS

A more complete appreciation of the invention and many of the attendant advantages thereof will be readily obtained as the same becomes better understood by reference to the detailed description when considered in connection with the accompanying drawings. Wherever possible, the same reference numbers will be used throughout the drawings to the same or the like parts. In the drawings.

DETAILED DESCRIPTION OF THE INVENTION

Figure 1:
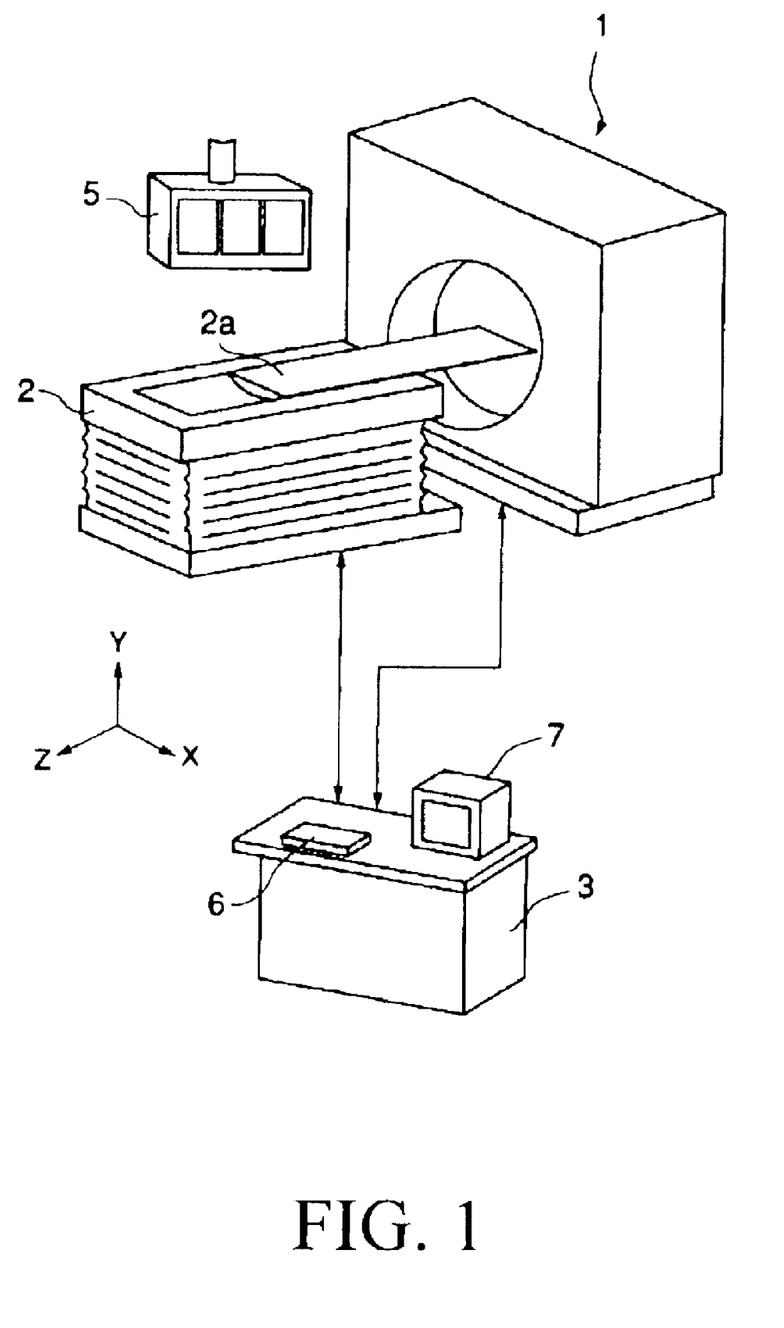
FIG. 1 is a perspective view of an X-ray CT apparatus of an embodiment according to the present invention.
Figure 2:
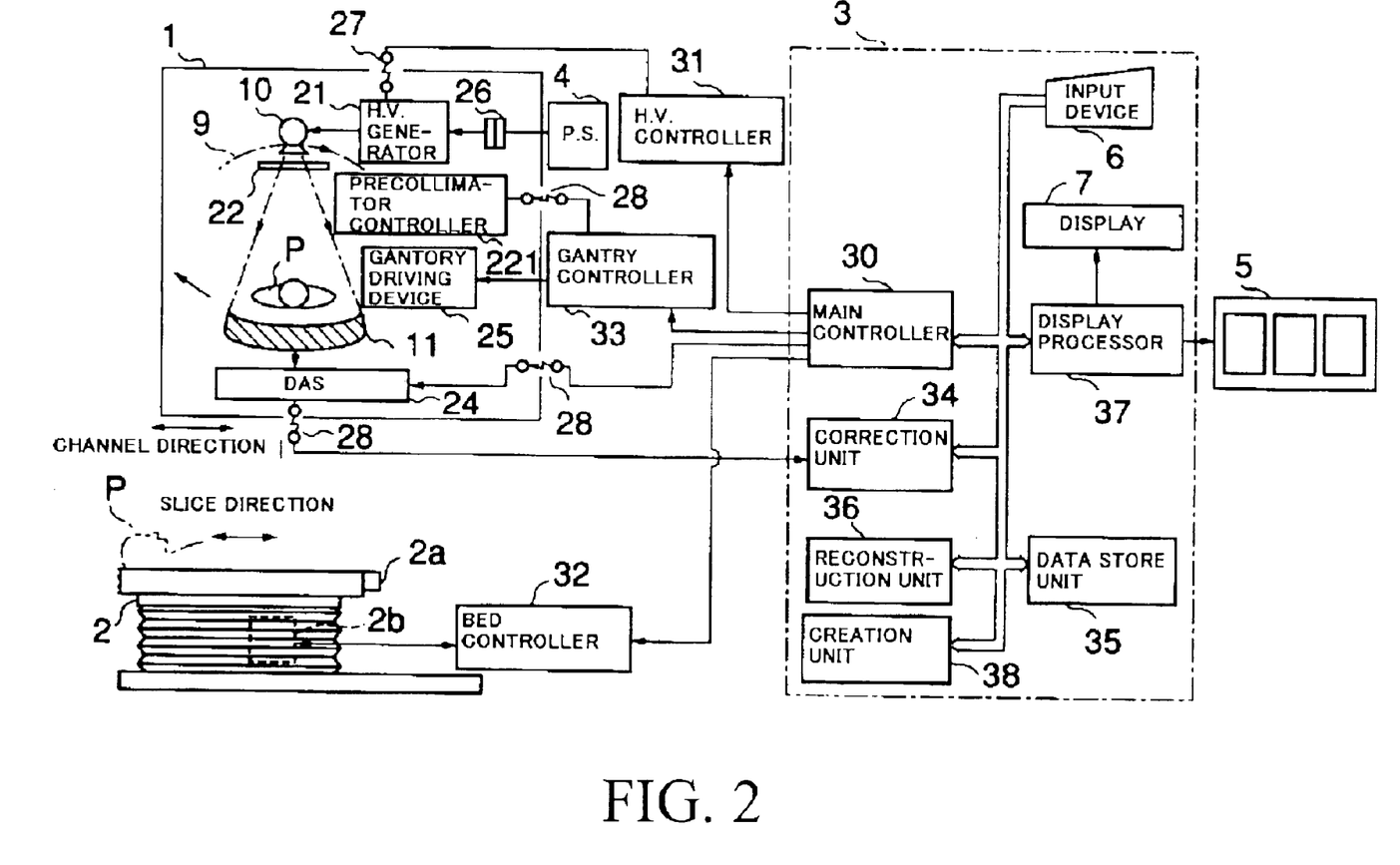
FIG. 2 is a block diagram of the X-ray CT apparatus of the embodiment illustrated in FIG. 1.

With reference to FIG. 1 and FIG. 2, the X-ray CT apparatus consistent with the invention includes a gantry 1, a bed 2, a control cabinet 3, an input device 6, a power supply 4, a displays 5 and 7, and various controllers 31 to 33, is driven by an R—R (Rotation-Rotation) system, for example. Further, the X-ray CT apparatus includes a high-voltage controller 31, a gantry controller 33, and a bed controller 32. A longitudinal direction of the bed 2 is defined as a slice direction Z. A direction of an X-ray radiation that is perpendicular to the slice direction Z is defined as an X-ray beam radiation direction Y, and a direction perpendicular to both of the slice direction and the X-ray beam radiation direction is defined as a channel direction X.

A top plate 2a of the bed 2 is slidably supported on the upper surface of the bed 2 to move along the slice direction Z. A patient P lies down on the top plate 2a. The top plate 2a is moved into a diagnostic opening of a gantry 1 by a bed driving device 2b, such as a servomotor. The bed driving device 2b receives a driving signal from a bed controller 32. The bed 2 includes a position detector, such as an encoder for detecting a position of the top plate 2a along the slice direction Z to output a corresponding electrical signal. The electrical signal is delivered to the bed controller 32 as a bed control signal.

The gantry 1 includes an approximately cylindrical rotation rotary frame. The diagnostic opening locates inside the rotary frame. In the rotary frame, an X-ray tube 10 and a multi-slice detector 11 are provided so as to face with each other. A patient P is positioned between the X-ray tube 10 and the detector 11, as shown in FIG. 2. A high-voltage generator 21, a precollimator 22, a precollimator controller 221, a data acquisition system (DAS) 24, and a gantry driving device 25 are equipped at predetermined positions on the rotary frame. The precollimator 22 has a variable-sized aperture along the slice direction Z to determine a beam width of X-ray radiated from the X-ray tube 10. The width of the aperture is varied by the precollimator controller 221. The X-ray tube 10 as an X-ray source is, for example, a rotary anode X-ray tube. A filament of the X-ray tube is heated by a current supplied from the high-voltage generator 21 so as to emit electrons toward the rotary anode as a target . The electrons impinge the target surface to form an effective focal point, and an X-ray beam (fan beam) is radiated from the portion of the effective focal point of the target surface. The high-voltage generator 21 receives a low-voltage power from a power supply device 4 via a low-voltage slip ring 26. It also receives an X-ray radiation control signal from the high-voltage controller 31 via an optical signal transmission system 27. Thus, the high-voltage generator 21 generates a high voltage from the received low-voltage power and generates a pulse-shaped tube voltage from the high voltage in accordance with the control signal. The pulse-shaped tube voltage is supplied to the X-ray tube 10.

Figure 3:
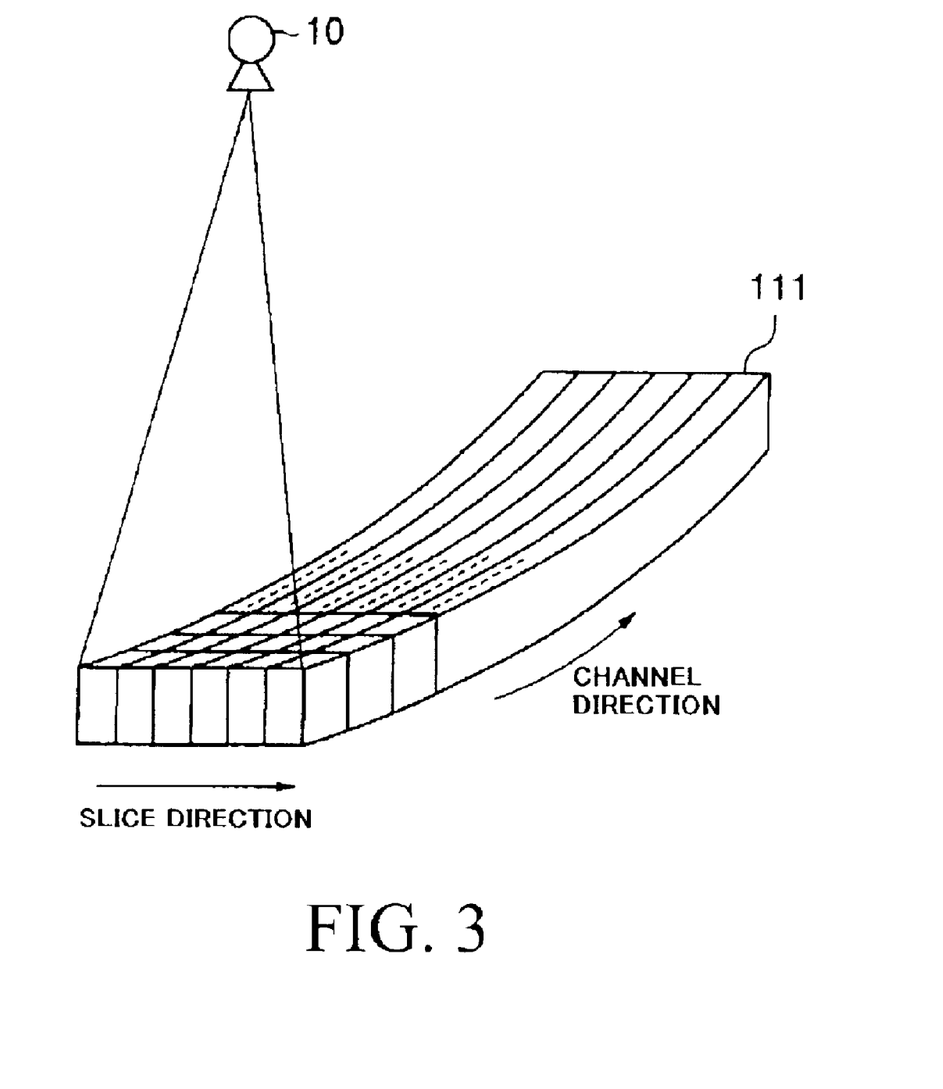
FIG. 3 explains a multi-slice X-ray detector of the embodiment in FIG. 1.

A multi-slice detector 11 comprises a two-dimensional detector that has a plurality of detection arrays, for example 16 arrays, in the slice direction Z, as illustrated in FIG. 3. Each detection array has a plurality of detection elements along the channel direction Y. The X-ray tube 10 and the X-ray detector 11 are rotatable around the rotation central axis of the diagnostic opening dependent upon the rotation of the rotary frame. Each detection element of the multi-slice detector 11 has a solid-state detector structure including a scintillator and photodiode for converting incoming transmitted X-ray into a corresponding current signal. A current signal detected by the multi-slice detector 11 is sent to a DAS 24. The DAS 24 amplifies the current signal and AID converts the amplified current signal. The converted signal is sent to a data transmission unit 28. The DAS 24 includes a data selection unit for selecting detection signals of one detection array from "N channels times F arrays" detection signals (N and F are positive integers larger than "1") in accordance with an array select signal. The DAS 24 bundles the detection signals in the slice direction Z. The DAS 24 amplifies and converts the bundled signals from an analog signal to a digital signal. The array select signal is supplied from a main controller 30. The data transmission unit 28 connects signal paths between a rotary unit and a stationary in the gantry 1. As the data transmission unit 28, an optical transmission system for transmitting signals in a non-contact manner is used.

A correction unit 34 performs various correction processes of the digital data supplied from the DAS 24 in accordance with a process command from a main controller 30. The corrected data is temporarily stored in a data store unit 35 in response to a write command from the main controller 30. The stored data is read out from the data store unit 35 in accordance with a read command from the main controller 30 at a desired timing. The read out data is transferred to a reconstruction unit 36 and a creation unit 38. Under the control of the main controller 30, the reconstruction unit 36 reconstructs the tomographic image on basis of the transferred data by a convolution back-projection method. The reconstruction unit 36 may reconstruct a plurality of tomographic images in a shorter time than a data acquisition time. The creation unit 38 creates a plane image in a particular direction based on the transferred data under the control of the main controller 30. The plane image is not reconstructed but is created based on a particular direction data. When the plan image is created, some correction, such as a fan-angle correction, may be performed. The transferred data to the reconstruction unit 36 may be different from the transferred data to the creation unit 38.

Under the control of the main controller 30, the tomographic image data and the plane image data are stored in a data store unit 35, dependent upon its necessity. They are also sent to a display processor 37. The display processor 37 performs required processes such as a color conversion process, a superposing process of annotation data and scan information, for the tomographic image data. The processed data is supplied to the display 5. The display processor 37 also performs required processes for the plane image data. The display 5 converts the tomographic image data and the plane image data from the digital data to the analog data in order to display both images on a monitor in a real time.

Figure 4:
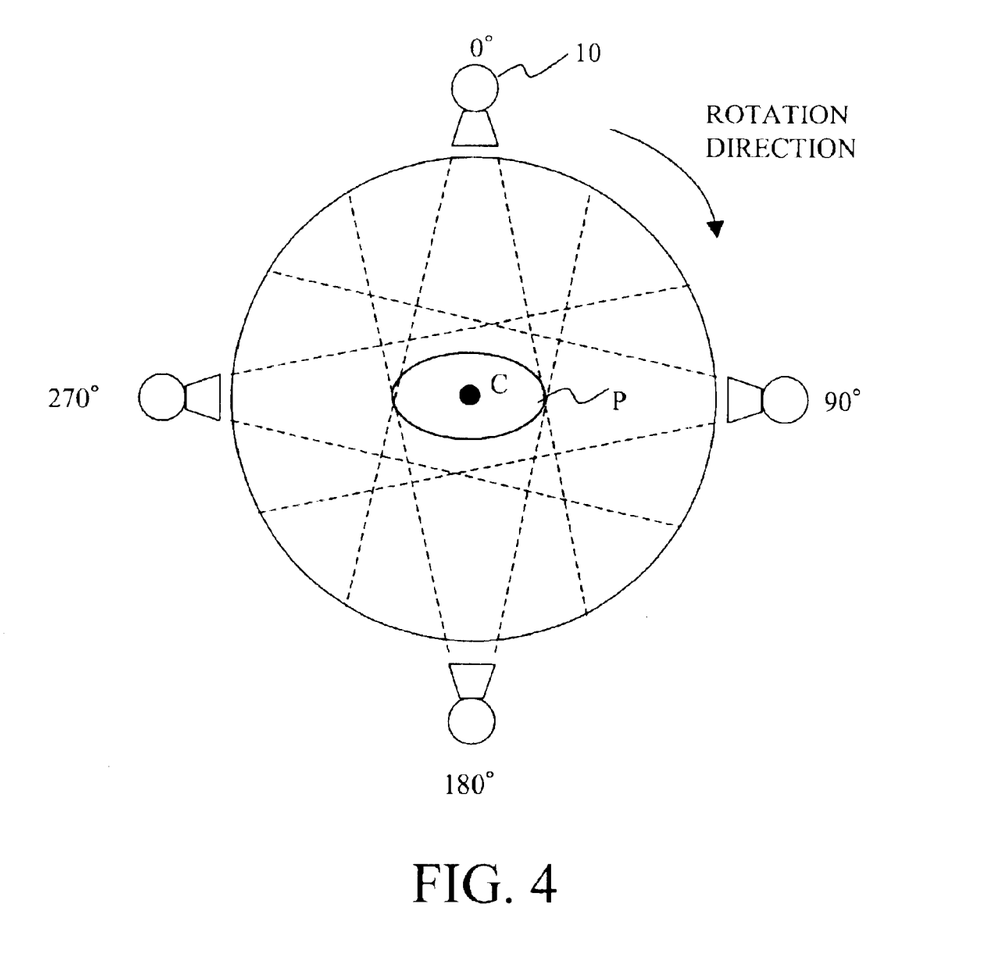
FIG. 4 explains a position of an X-ray tube and a direction of a plane image.

An input device 6 allows an operator to input various kinds of designation of scan conditions such as the number and locations of detection arrays of the X-ray detector, scan portion and position, slice thickness, X-ray tube voltage and current, plane imaging direction, the number of plane images, and the image display conditions. The plane imaging direction indicates a plurality of observing directions of the plane image from the operator. As illustrated in FIG. 4, in this embodiment, the number of plane images is observed from four directions, for instance, 0, 90, 180, 270 degrees.

An operator stands besides a patient and operates the needle, observing a display 5 near a gantry 1. Before the operator inserts the needle to the patient, the operator inputs the scan conditions by an input device 6, such that the needle is displayed on the display 5. FIG. shows monitor view as one example when an imaging portion is a patient's breast. Suppose a slice width of a detection array in a slice direction Z is 0.5 mm, an inputted slice thickness is 2.0 mm and an inputted number of detection arrays is 16 as the scan conditions, a number of tomographic images is sets as four, i.e., A through D. The number of tomographic images is transmitted to a DAS 24. The inputted X-ray tube voltage and current as the scan conditions are transmitted to an X-ray tube 10 to be controlled via a high-voltage controller 31 and a high-voltage generator 21. Inputted scan portion and position as the scan conditions are transmitted to a precollimator controller 221 and the DAS 24 to be controlled. The operator sets a number of plane images and a respective direction, considering an insertion direction of the needle. In this embodiment, 0-degree, 90-degrees, 180-degrees, 270-degrees are taken, for example. The information about these number and direction is transmitted to a creation unit 38.

Figure 5:
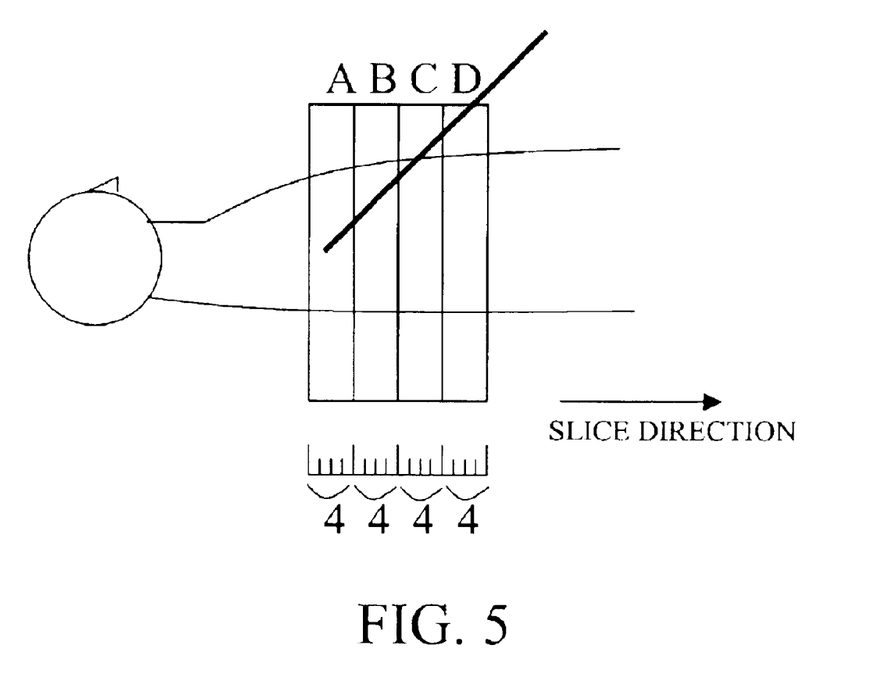
FIG. 5 explains an insertion of a needle into an object.

In a real imaging, controlled by a gantry driving device 25 and a gantry controller 33, the X-ray tube 10 rotates around a rotation axis C along the slice direction Z as shown in FIG. 4 that is an illustration from a leg direction of a patient P. In this embodiment, a front direction of the patient P is 0 degree, a left hand direction is 90 degrees, a back direction is 180 degrees, and a right hand direction is 270 degrees. In the real imaging of this embodiment, a position of the X-ray tube is not changed in the slice direction Z. Thus, a top plate 2a is controlled to be fixed by a bed controller 32. In this real imaging, a dynamic scan is performed for continuously imaging the same position of the patient P in the slice direction Z. Acquired data by the real imaging is transmitted to a reconstruction unit 36 and a creation unit 38 via a correction unit 34 and a data store unit 35. The data transmitted to the reconstruction unit 36 becomes whole directions, 360 degrees, data, as illustrated in FIG. 5, areas A to C. The reconstruction unit 36 reconstructs three tomographic images corresponding to the areas A through C. On the other hand, the transmitted data to the creation unit 38 is only specific direction data, such as 0 degree, 90 degrees, 180 degrees, 270 degrees. The creation unit 38 creates four plane images corresponding to each areas A through D. In this embodiment, a number of detection arrays for the plane images is larger than that for the tomographic images. Thus, data acquisition range for the plane images (A to D) in the slice direction Z is larger than that for the tomographic images (A to C). Even if the data acquisition range for the tomographic images is narrow, for instance, a slice thickness is small, wide plane image can be created in the slice direction Z. These data (A to C, 0 degree, 90 degrees, 180 degrees, 270 degrees data) is used for both of the tomographic images and the plane images.

Figure 6:
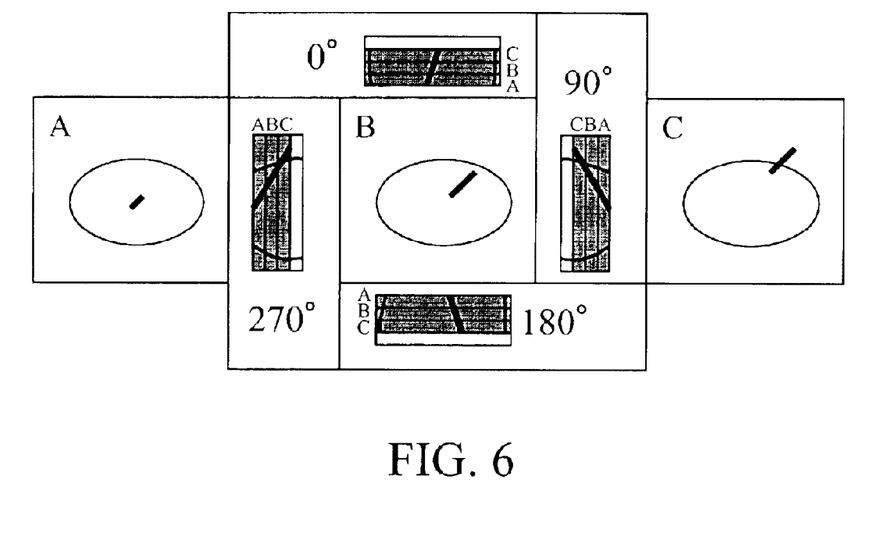
FIG. 6 is a displayed view on a monitor of the inserted needle into the object.

The tomographic images and the plane images are displayed on a display 5 and 7 via a display processor 37. FIG. 6 shows a display on the monitor 5. In central three areas in a line, three tomographic images A, B and C are displayed. Four plane images are arranged around the central tomographic image B. The created plane image is displayed on an upper side of the central tomographic image B, based on the acquired data when the X-ray tube 10 is positioned at 0 degree. Similarly, a right side image is 90 degrees image, a down side image is 180 degrees image, and a left side image is 270 degrees image. As shown in FIG. 6, an area of the tomographic images A to C may be distinctly displayed in comparison with non-tomographic image area D by a color. In this case, an operator can easily understand the tomographic image area Further, as shown in FIG. 6, a respective position of the tomographic images A to C may also be distinctly displayed by an alphabet, such as A, B and C. In this case, the operator can easily understand a relationship between the tomographic images and plane images.

Figure 7A:
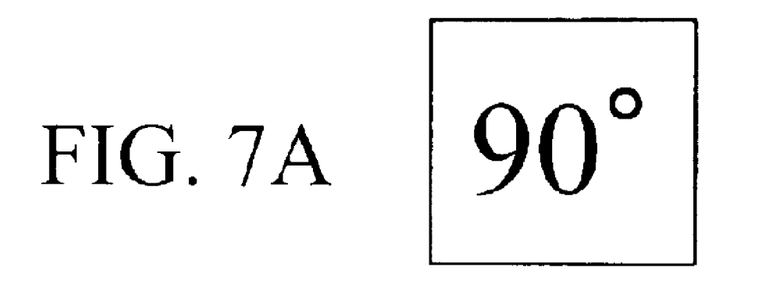
FIG. 7A is an example of an indicating direction of a plane image.
Figure 7B:
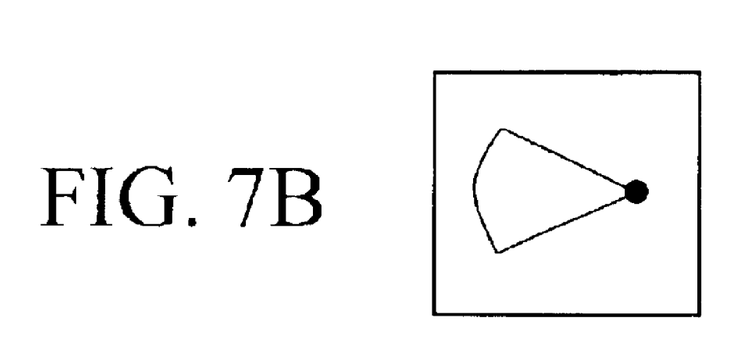
FIG. 7B is another example of indicating direction of a plane image.
Figure 7C:
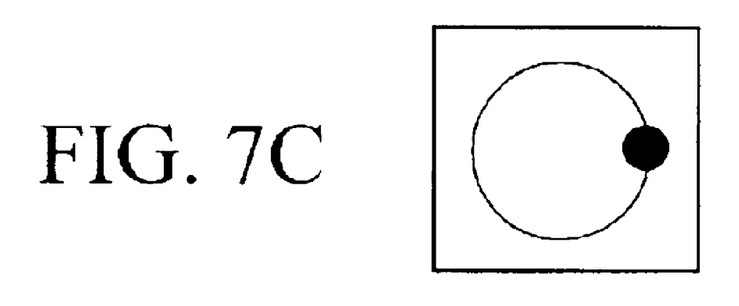
FIG. 7C is still other example of indicating direction of a plane image.

FIG. 7A to 7C illustrate examples of indicating direction of the plane images. FIG. 7A shows an example that indicates the plane image direction by numeric character. FIG. 7B indicates the plane image direction by a view showing a position of an X-ray tube and a range of an radiated X-ray. FIG. 7C indicates the plane image direction by a view showing a position of an X-ray tube and a gantry circle. The plane image direction may be changed while the X-ray is radiated.

Figure 8A:
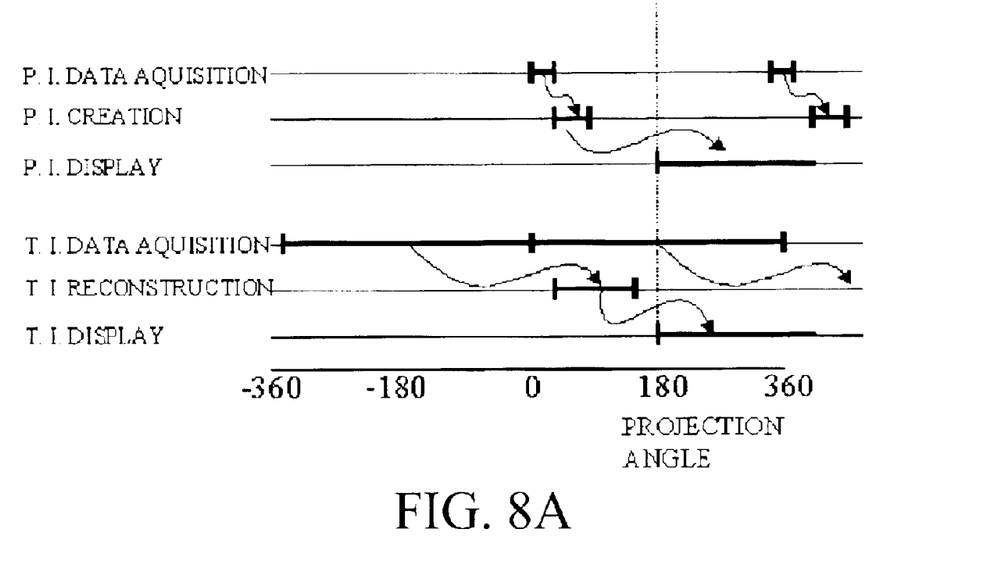
FIG. 8A is a timing chart showing the plane image and a synchronously displayed tomographic image.

The tomographic image and plane image are made in a real time. In order to simplify the explanation, the following is explained as to 0 degree plane image direction. The display timing of each image will be explained as two patterns. In a first pattern, as illustrated in FIG. 8A, the tomographic image is synchronized with the plane image. A top line shows a data acquisition term for the plane image. The data acquisition term starts from when an X-ray is radiated and ends when data is stored in a data store unit 35. Since the acquired data is not all 360 degrees data but specific direction data near 0 degree, it takes a short term. The next line shows a creation term for the plane image. The creation term is starts from when data is read out from the data store unit 35 and ends when the creation of the plane image is completed. The third line shows a display term for the plane image. Similarly, the forth line shows a data acquisition term for the tomographic image. Since the acquired data is all 360 degrees data, it takes a longer term than that for the plane image. The fifth line shows a reconstruction term for the tomographic image. The reconstruction term starts from when data is read out from the data store unit 35 and ends when the reconstruction of the tomographic image is completed. Since a convolution backprojection process is executed in the reconstruction, in general, it takes a longer term than the creation of the plane image. Thus, a term for preparing the display of the tomographic image is different from that of the plane image. As one example, display synchronization between the tomographic image and the plane image is executed as shown in FIG. 8A by a dotted line. Consequently, both images are simultaneously displayed. This means that the display of the plane image is delayed until the tomographic image is prepared. As a result, since both images are simultaneously updated, an operator can easily observe both images.

Figure 8B:
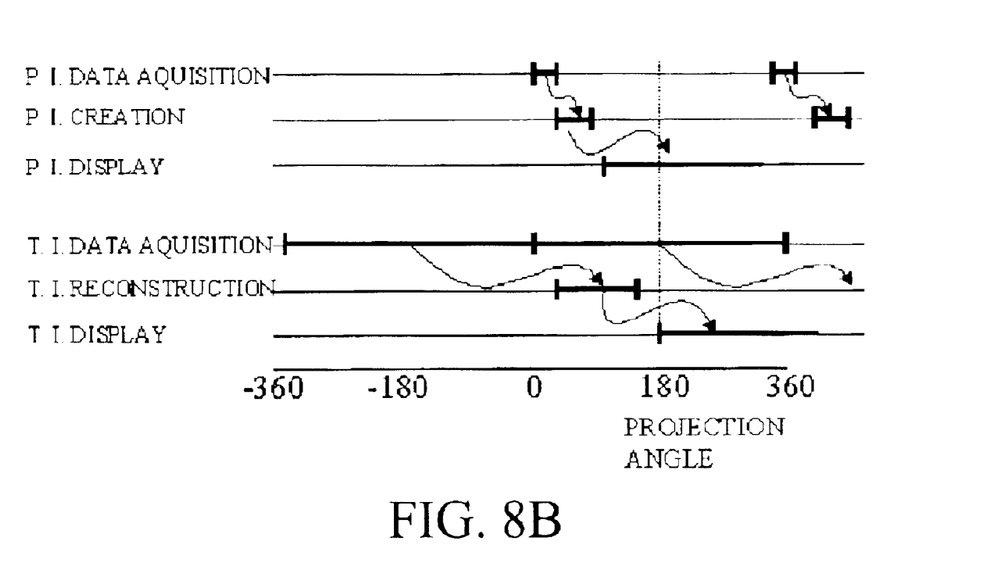
FIG. 8B is a timing chart showing the plane image and an asynchronously displayed tomographic image.

As a second pattern, FIG. 8B shows that the tomographic image is asynchronized with the plane image. In FIG. 8B, the plane image is asynchronously displayed regardless of the tomographic image. That is, each images is independently updated. In this example, the plane image is updated more frequently than that of the tomographic image. When each image is independently updated as this example, the operator can observe a state of a needle insertion in a more real time. Although, in the above examples, a synchronous or asynchronous display timing is explained, an image making timing, may be synchronized.

The invention may be applied in various modifications.
1. Type of CT

In the above embodiment, a third-generation CT apparatus, i.e., the X-ray tube and detector synchronously move around the patient, has been explained, but the present invention may be applied to other X-ray CT apparatus. For instance, the present invention may also be applied to fourth-generation CT apparatus in which the X-ray detector is laid out in a cylindrical pattern, and the X-ray tube rotates, and to fifth-generation CT in which an electron beam impinges against a fixed target laid out in a ring or cylindrical pattern to generate X-rays, which are received by a fixed detector. The present invention may also be applied to a multi X-ray tube CT apparatus which has a plurality of X-ray tubes, such as three tubes and corresponding X-ray detectors. In such a case, both of the plane image and the tomographic image can be created more frequently.

2. Type of Detector (256 Arrays, Surface Detector)

In the above embodiment, the X-ray CT apparatus having 16 detection arrays has been exemplified. However, other number of detection arrays may be used. For example, the present invention may be applied to an X-ray CT apparatus having a 256 arrays multi-slice detector, and may also be applied to an X-ray CT apparatus that uses a surface detector such as an image intensifier.

3. Reconstruction Method

In the present invention, various types of reconstruction methods may be applied. For example, a reconstruction method that makes normal filter back-projection regardless of the angle of an X-ray beam, i.e., cone angle, in the rotation axis direction may be used. Or a reconstruction method that reconstructs an image by back-projecting acquired data based on their acquisition route in accordance with the cone angle may be used. In this case, acquired data of the respective arrays are not bundled by the aforementioned correction unit, but an image with a slice thickness designated upon reconstruction is reconstructed. In this manner, image quality of reconstructed images using a larger number of detection arrays can be improved. Further, in the above embodiment, although a case where an image is reconstructed from 360 degrees data has been explained, a half reconstruction method using about 180 degrees (180 degrees+a fan angle) data or a partial reconstruction method using partial data acquired by a predetermined angle, may be used.

4. Plane Image Creation Method

In the above embodiment, a case where a plane image at 0 degree is different from a plane image at 180 degrees has been explained. However one plane image is approximately reversed to the other image. Therefore, a reversed plane image may be treated as the same image as an opposite plane image. In this case, a plane image can be newly displayed by a half time. When the operator sets a plane image direction is 0 degree, the plane image is also updated at 180 degrees. By using this reverse plane image creation method, the plane image can be updated more frequently. Further, in the above embodiment, an operator sets the plane image direction and its number, but the plane image direction or its number may be fixed in advance. Or a needle detector for automatically detecting an inserted direction of the needle may be provided to determine the plane image direction.

5. Display Method

In the above embodiment, a tomographic image and a plane image are displayed synchronously or the plane image is asynchronously displayed more frequently than the tomographic image is displayed. However the present invention may use other display method. For example, by using a fast reconstruction method, such as a half reconstruction method or a partial reconstruction method, the display of the tomographic image may be faster than that of the plane image. Or by using 180 degrees plane image creation method as described above, the plane image may be displayed more frequently than the tomographic image is displayed.

In the above embodiment, plane images are displayed around one of tomographic images, but other display method may be applied. For example, the plane images may be displayed at least one of up side, down side, right side and left side of the tomographic image. Further, in the above embodiment, two plane images are positioned at two places between three tomographic images, however one plane image may be positioned at least one place between three tomographic images.

In the above embodiment, all images are displayed on the single display. However, the present invention may be applied to other image display method. For example, a plurality of images may be respectively displayed on independent displays. In this manner, the display areas of the individual images can be broadened. Also, a projector type display may be used. In this case, images can be displayed in a very enlarged scale and can be observed more easily. Furthermore, a head-mounted display (HMD) may be used. In such case, since images are displayed within the range of the field of view independently of the direction in which the operator faces, the operator needs not to look back to observe the display during the operation procedures, and the load on the operator can be reduced, thus improving operability.

6. Location of Bundling

In the above embodiment, a unit for bundling data is the correction unit 34, but the present invention may be applied to other unit. For example, a data acquisition system (DAS) 24 may execute a process pertaining to data bundling, or image bundling after individual images are reconstructed.

7. Superposed Display of Image

In the above embodiment, a plurality of images are displayed in a line. However, the present invention may use other image display method. For example, three images having different slice positions may be generated in correspondence with R, G, and B, and may be superposed to display a single image. In this case, three images are taken as an example, but the number of images may not be three. The present invention may be applied to two images or four or more images.

8. Number of images

Figure 9:
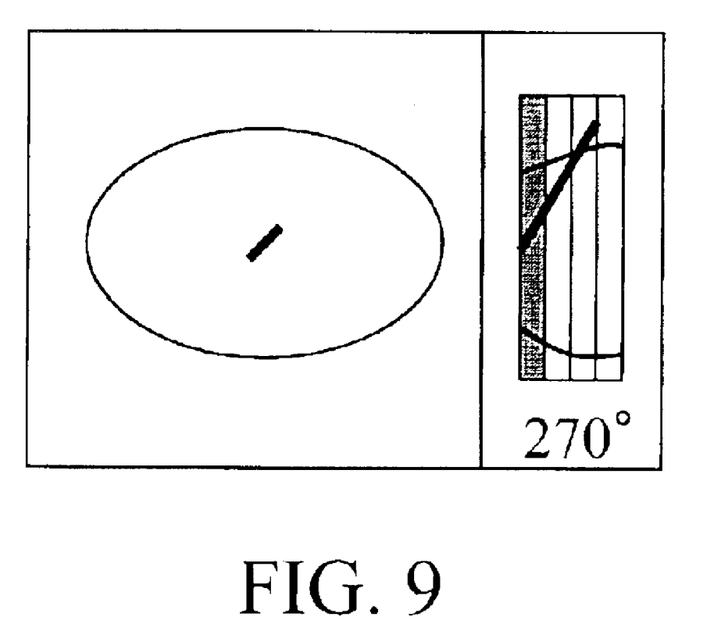
FIG. 9 is a monitor view of a needle insertion according to another embodiment consistent with the invention.

In the above embodiment, three tomographic images and four plane images are reconstructed or created, however one tomographic image and one plane image may be reconstructed or created. FIG. 9 shows a monitor view in this case. In other embodiment, a function which can switch the plane image ON/OFF or can changes the display of the tomographic image to that of the plane image and vice versa, may be provided. Further, a function which can change a number of tomographic or plane images may be provided.

The present invention is not limited to the above embodiments, and various modifications may be made without departing from the spirit or scope of the general inventive concept. A function which is executed by hardware in the above embodiment, may be executed by software. For example, in the above embodiment, a tomographic image is reconstructed by the reconstruction unit 36, but the reconstruction may be executed by software using a general personal computer.

What is claimed is:

1. An X-ray computed tomography apparatus, comprising:

an X-ray source configured to radiate an X-ray toward an object;

an X-ray detection unit configured to detect the X-ray through the object and to generate a corresponding signal;

a data acquisition unit configured to acquire data based on the corresponding signal;

a reconstruction unit configured to continuously reconstruct a tomographic image of the object based on a predetermined term based on the acquired data;

a creation unit configured to continuously create a plane image of the object by a predetermined term based on the acquired data;

a display unit configured to display both the tomographic image and the plane image;

wherein the X-ray detection unit comprises detection arrays arranged in a first direction along a body axis of the object and a second direction perpendicular to the first direction and an X-ray radiation direction;

wherein the X-ray detection unit continuously detects the X-ray through the same position of the object in the first direction; and wherein a number of the detection arrays for creating the plane images is four and a number of the detection arrays for reconstructing the tomographic images is three.

2. The X-ray computed tomography apparatus according to claim 1, wherein the display unit displays both the tomographic image and the plane image each time when the reconstruction unit reconstructs the tomographic image and the creation unit creates the plane image.

3. The X-ray computed tomography apparatus according to claim 1, wherein the display unit synchronously displays the tomographic image and the plane image.

4. The X-ray computed tomography apparatus according to claim 1, wherein the display unit asynchronously displays the tomographic image and the plane image.

5. The X-ray computed tomography apparatus according to claim 1, wherein the reconstruction unit synchronously reconstructs the tomographic image with the plane image.

6. The X-ray computed tomography apparatus according to claim 1, wherein the reconstruction unit reconstructs a plurality of tomographic images in the first direction.

7. The X-ray computed tomography apparatus according to claim 1, wherein the creation unit creates a plurality of plane images from a plurality of directions.

8. The X-ray computed tomography apparatus according to claim 1 wherein the display unit displays an area of the tomographic image on the plane image.

9. The X-ray computed tomography apparatus according to claim 1, wherein:

the reconstruction unit reconstructs a plurality of tomographic images in the first direction; and the display unit displays a respective position of each of the tomographic image on the plane image.

10. The X-ray computed tomography apparatus according to claim 1, wherein the display unit displays the plane image each time the X-ray radiation direction changes about 180 degrees.

11. The X-ray computed tomography apparatus according to claim 1, wherein the display unit displays the plane image each time the X-ray radiation direction changes about 360 degrees.

12. The X-ray computed tomography apparatus according to claim 1, wherein the display unit displays the plane image around the tomographic image.

13. The X-ray computed tomography apparatus according to claim 1, wherein the display unit displays the plane images on at least one side of the right and left sides of the tomographic image.

14. The X-ray computed tomography apparatus according to claim 1, wherein the display unit displays the plane images on at least one side of the upper and lower sides of the tomographic image.

15. The X-ray computed tomography apparatus according to claim 1, wherein:

the reconstruction unit reconstructs three tomographic images in the first direction; and the display unit displays the three tomographic images arranged in a line.

16. The X-ray computed tomography apparatus according to claim 15, wherein the display unit displays the plane image on at least one of two places between the three tomographic images.

17. The X-ray computed tomography apparatus according to claim 1, further comprising an input unit to input a direction of the plane image.

18. The X-ray computed tomography apparatus according to claim 1, further comprising a control unit configured to control a direction of the plane image according to an inserted direction of a needle into the object.

19. The X-ray computed tomography apparatus according to claim 1, wherein the display unit displays the tomographic image more frequently than the plane image.

20. The X-ray computed tomography apparatus according to claim 1, wherein the display unit displays the plane image more frequently than the tomographic image.

21. An X-ray computed tomography apparatus, comprising:

an X-ray source configured to radiate an X-ray toward an object;

an X-ray detection unit configured to detect the X-ray through the object and to generate a corresponding signal;

a data acquisition unit configured to acquire data based on the corresponding signal; a reconstruction unit configured to reconstruct a tomographic image of the object based on the acquired data;

an input unit to input a direction of a plane image of the object;

a creation unit configured to create the plane image based on the acquired data according to the direction of the plane image;

wherein the X-ray detection unit comprises detection arrays arranged in a first direction along a body axis of the object and a second direction perpendicular to the first direction and an X-ray radiation direction;

wherein the X-ray detection unit continuously detects the X-ray through the same position of the object in the first direction; and wherein a number of the detection arrays for creating the plane images is four and a number of the detection arrays for reconstructing the tomographic images is three.

22. The X-ray computed tomography apparatus according to claim 21, wherein the display unit displays the direction of the plane image.

23. The X-ray computed tomography apparatus according to claim 22, wherein the input unit comprises an input element configured to change the direction of the plane image while the X-ray source radiates the X-ray.

24. An X-ray computed tomography apparatus, comprising:

an X-ray source configured to radiate an X-ray toward an object;

a rotation unit configured to rotate a focal point of the X-ray;

an X-ray detection unit configured to detect the X-ray through the object and to generate a corresponding signal;

a data acquisition unit configured to acquire data based on the corresponding signal while the focal point of the X-ray rotates;

a reconstruction unit configured to reconstruct a tomographic image of the object based on the acquired data;

a creation unit configured to create a plane image of the object based on the acquired data;

wherein the X-ray detection unit comprises detection arrays arranged in a first direction along a body axis of the object and a second direction perpendicular to the first direction and an X-ray radiation direction;

wherein the X-ray detection unit continuously detects the X-ray through the same position of the object in the first direction; and wherein a number of the detection arrays for creating the plane images is four and a number of the detection arrays for reconstructing the tomographic images is three.

25. An X-ray computed tomography apparatus, comprising:

an X-ray source configured to radiate an X-ray toward an object;

an X-ray detection unit configured to detect the X-ray through the object and to generate a corresponding signal;

a data acquisition unit configured to acquire data based on the corresponding signal;

a reconstruction unit configured to reconstruct a tomographic image of the object based on the acquired data;

a creation unit configured to create a plane image of the object based on the acquired data including a part of data used for the tomographic image;

wherein the X-ray detection unit comprises detection arrays arranged in a first direction along a body axis of the object and a second direction perpendicular to the first direction and an X-ray radiation direction;

wherein the X-ray detection unit continuously detects the X-ray through the same position of the object in the first direction; and wherein a number of the detection arrays for creating the plane images is four and a number of the detection arrays for reconstructing the tomographic images is three.

26. A method for controlling an X-ray computed tomography apparatus, comprising:

radiating an X-ray toward an object by an X-ray source;

detecting the X-ray through the object to generate a corresponding signal by an X-ray detection unit;

acquiring data based on the corresponding signal by a data acquisition unit;

continuously reconstructing a tomographic image of the object by a predetermined term based on the acquired data by a reconstruction unit;

continuously creating a plane image of the object by a predetermined term based on the acquired data by a predetermined term by a creation unit;

wherein the X-ray detection unit comprises detection arrays arranged in a first direction along a body axis of the object and a second direction perpendicular to the first direction and an X-ray radiation direction;

wherein the X-ray detection unit continuously detects the X-ray through the same position of the object in the first direction; and wherein a number of the detection arrays for creating the plane images is four and a number of the detection arrays for reconstructing the tomographic images is three.

* * * * *